United States Patent
Ironi et al.

(10) Patent No.: US 10,213,602 B2
(45) Date of Patent: Feb. 26, 2019

(54) TREATMENT OF HEADACHES BY ELECTRICAL STIMULATION

(71) Applicant: THERANICA BIO-ELECTRONICS LTD., Netanya (IL)

(72) Inventors: Alon Ironi, Haifa (IL); Ronen Jashek, Shoham (IL); Hamutal Raab, Hod Hasharon (IL); Amnon Harpak, Holon (IL); Shmuel Goldfisher, Petach Tikva (IL); Ilan Ovadia, Rishon Lezion (IL); Avner Taieb, Petach Tikva (IL); Lana Volokh, Haifa (IL); Tomer Yablonka, Tel Aviv (IL)

(73) Assignee: Theranica Bio-Electronics Ltd., Netanya (IL)

( * ) Notice: Subject to any disclaimer, the term of this patent is extended or adjusted under 35 U.S.C. 154(b) by 0 days.

(21) Appl. No.: 15/542,553

(22) PCT Filed: Jan. 11, 2016

(86) PCT No.: PCT/IB2016/050104
§ 371 (c)(1),
(2) Date: Jul. 10, 2017

(87) PCT Pub. No.: WO2016/113661
PCT Pub. Date: Jul. 21, 2016

(65) Prior Publication Data
US 2017/0368344 A1    Dec. 28, 2017

Related U.S. Application Data

(60) Provisional application No. 62/102,606, filed on Jan. 13, 2015.

(51) Int. Cl.
*A61N 1/36* (2006.01)
*A61N 1/04* (2006.01)
*A61N 1/372* (2006.01)

(52) U.S. Cl.
CPC ....... *A61N 1/36021* (2013.01); *A61N 1/0456* (2013.01); *A61N 1/0492* (2013.01); *A61N 1/36031* (2017.08); *A61N 1/37264* (2013.01)

(58) Field of Classification Search
None
See application file for complete search history.

(56) References Cited

U.S. PATENT DOCUMENTS

| | | |
|---|---|---|
| 4,613,850 A | 9/1986 | Timmermann |
| 4,785,813 A | 11/1988 | Petrofsky |
| 4,811,742 A | 3/1989 | Hassel et al. |
| 5,330,515 A | 7/1994 | Rutecki et al. |
| 6,217,574 B1 | 4/2001 | Webster |
| 6,741,889 B1 | 5/2004 | Holcomb |

(Continued)

FOREIGN PATENT DOCUMENTS

| | | |
|---|---|---|
| WO | 2005/039693 | 5/2005 |
| WO | 2015/042365 | 3/2015 |

(Continued)

OTHER PUBLICATIONS

An International Search Report and a Written Opinion both dated Apr. 24, 2017, which issued during the prosecution of Applicant's PCT/IL2017/050028.

(Continued)

*Primary Examiner* — Brian T Gedeon
(74) *Attorney, Agent, or Firm* — McDonnell Boehnen Hulbert & Berghoff LLP

(57) ABSTRACT

Systems and methods are described, including a system for electrostimulation. The system includes a patch (22), including a plurality of electrodes (24a, 24b), and a mobile device (28). A processor (30) of the mobile device is configured to receive an input from a subject (20) that indicates that the subject is experiencing a headache, and, in response to the input, while the patch is coupled to the subject, wirelessly communicate a control signal that causes the electrodes to stimulate the subject. Other embodiments are also described.

24 Claims, 1 Drawing Sheet

(56) References Cited

U.S. PATENT DOCUMENTS

| | | | |
|---|---|---|---|
| 7,221,980 | B2 | 5/2007 | Kotlik et al. |
| 8,340,771 | B2 | 12/2012 | Thimineur et al. |
| 8,428,734 | B2 | 4/2013 | Rigaux et al. |
| 8,478,420 | B2 | 7/2013 | Armstrong et al. |
| 8,620,434 | B2 | 12/2013 | Bodlaender et al. |
| 8,712,546 | B2 | 4/2014 | Kim et al. |
| 8,768,428 | B2 | 7/2014 | Clare et al. |
| 8,805,548 | B2 | 8/2014 | Mignolet et al. |
| 8,874,205 | B2 | 10/2014 | Simon et al. |
| 8,874,227 | B2 | 10/2014 | Simon et al. |
| 8,880,173 | B2 | 11/2014 | DiUbaldi et al. |
| 8,996,115 | B2 | 3/2015 | Trier et al. |
| 9,011,355 | B2 * | 4/2015 | Ehrenreich ............... A61H 1/00 381/151 |
| 9,067,054 | B2 | 6/2015 | Simon et al. |
| 9,138,580 | B2 | 9/2015 | Ignagni et al. |
| 9,205,256 | B2 | 12/2015 | Koo |
| 9,242,085 | B2 * | 1/2016 | Hershey ............... A61N 1/0456 |
| 9,242,092 | B2 | 1/2016 | Simon et al. |
| 9,248,279 | B2 | 2/2016 | Chen et al. |
| 9,333,347 | B2 | 5/2016 | Simon et al. |
| 9,375,571 | B2 | 6/2016 | Errico et al. |
| 9,415,219 | B2 | 8/2016 | Simon et al. |
| 2002/0138116 | A1 | 9/2002 | Bertolucci |
| 2004/0015212 | A1 | 1/2004 | Huber et al. |
| 2004/0030360 | A1 | 2/2004 | Eini et al. |
| 2005/0182457 | A1 | 8/2005 | Thrope et al. |
| 2005/0251061 | A1 | 11/2005 | Schuler et al. |
| 2006/0155345 | A1 | 7/2006 | Williams et al. |
| 2007/0123952 | A1 | 5/2007 | Strother et al. |
| 2007/0203534 | A1 | 8/2007 | Tapper |
| 2008/0033504 | A1 * | 2/2008 | Bertolucci ........... A61H 39/002 607/46 |
| 2008/0065182 | A1 | 3/2008 | Strother et al. |
| 2009/0182393 | A1 | 7/2009 | Bachinski et al. |
| 2011/0112605 | A1 | 5/2011 | Fahey |
| 2011/0264171 | A1 | 10/2011 | Torgerson |
| 2012/0184801 | A1 * | 7/2012 | Simon ..................... A61N 2/006 600/14 |
| 2013/0093501 | A1 | 4/2013 | Kajimoto |
| 2013/0158627 | A1 | 6/2013 | Gozani et al. |
| 2013/0245486 | A1 | 9/2013 | Simon et al. |
| 2013/0338729 | A1 | 12/2013 | Spector |
| 2014/0031895 | A1 | 1/2014 | Rahimi et al. |
| 2014/0148870 | A1 | 5/2014 | Burnett |
| 2014/0194946 | A1 | 7/2014 | Thomas et al. |
| 2014/0222102 | A1 | 8/2014 | Lemus et al. |
| 2014/0249601 | A1 | 9/2014 | Bachinski et al. |
| 2014/0296934 | A1 | 10/2014 | Gozani et al. |
| 2014/0324120 | A1 | 10/2014 | Bogie et al. |
| 2014/0371814 | A1 | 12/2014 | Spizzirri et al. |
| 2015/0005852 | A1 | 1/2015 | Hershey et al. |
| 2015/0148878 | A1 | 5/2015 | Yoo et al. |
| 2015/0174406 | A1 | 5/2015 | Lamensdorf et al. |
| 2015/0165186 | A1 | 6/2015 | Dar et al. |
| 2015/0257970 | A1 | 9/2015 | Mucke et al. |
| 2017/0001003 | A1 | 1/2017 | Pivonka et al. |
| 2017/0197077 | A1 | 7/2017 | Harpak et al. |

FOREIGN PATENT DOCUMENTS

| | | |
|---|---|---|
| WO | 2016113661 | 7/2016 |
| WO | 2016/125087 | 8/2016 |
| WO | 2016/135604 | 9/2016 |
| WO | 2016/203356 | 12/2016 |
| WO | 2017/051412 | 3/2017 |
| WO | 2017/122195 | 7/2017 |

OTHER PUBLICATIONS

Degen et al., "An improved Method to continuously monitor the Electrode-Skin Impedance during Bioelectric Measurements", Proceedings of the 29th Annual International Conference of the IEEE EMBS Cite Internationale, Lyon, France, pp. 6294-6297, Aug. 23-26, 2007.

An International Search Report and a Written Opinion both dated Apr. 20, 2016, which issued during the prosecution of Applicant's PCT/IB2016/050104.

An Office Action dated Mar. 6, 2017, which issued during the prosecution of U.S. Appl. No. 14/992,046.

Notice of Allowance dated Oct. 27, 2017, which issued during the prosecution of U.S. Appl. No. 14/992,046

Slavin, Konstantin V., Hrachya Nersesyan, and Christian Wess. "Peripheral neurostimulation for treatment of intractable occipital neuralgia." Neurosurgery 58.1 (2006): 1 12-119.

Ristic, Dejan, and Jens Eilrich. "Innocuous peripheral nerve stimulation shifts stimulus-response function of painful laser stimulation in man." Neuromodulation: Technology at the Neural Interface 17.7 (2014): 686-695.

Nir, Rony-Reuven, et al. "A psychophysical study of endogenous analgesia: the role of the conditioning pain in the induction and magnitude of conditioned pain modulation." European Journal of Pain 15.5 (2011): 491-497.

Burstein, Rami, Michael F. Cutrer, and David Yarnitsky. "The development of cutaneous allodynia during a migraine attack clinical evidence for the sequential recruitment of spinal and supraspinal nociceptive neurons in migraine." Brain 123.8 (2000): 1703-1709.

Johnson MI. Transcutaneous electrical nerve stimulation (TENS) and TENS-like devices: Do they provide pain relief? Journal of Pain 2001;8:121-58.

Melzack R. Prolonged relief of pain by brief, intense transcutaneosomatic stimulation. Journal of Pain. 1975;1:357-73.

Bowman BR, Baker LL. Effects of waveform parameters on comfort during transcutaneous neuromuscular electrical stimulation. Annals of Biomedical Engineering. 1985;13:59-74.

Walsh DM, Foster NE, Baxter GD, Allen JM. Transcutaneous electrical nerve stimulation. relevance of stimulation parameters to neurophysiological and hypoalgesic effects. American Journal of Physical Medicine and Rehabilitation. 1995;74: 199-206.

Petrofsky JS, Suh HJ, Gunda S, Prowse M, Batt J. Interrelationships between body fat and skin blood flow and the current required for electrical stimulation of human muscle. Medical Engineering & Physics. 2008;30: 931-6.

Gopalkrishnan P, Sluka KA. Effect of varying frequency, intensity, and pulse duration of transcutaneous electrical nerve stimulation on primary hyperalgesia in inflamed rats. Archives of Physical Medicine and Rehabilitation. 2000;81: 984-90.

Han JS, Chen XH, Sun SL, Xu XJ, Yuan Y, Yan SC, Hao JX, Terenius L. Effect of low- and high-frequency TENS on Met-enkephalin-Arg-Phe and dynorphin A immunoreactivity in human lumbar CSF. Journal of Pain, vol. 47, Issue 3, Dec. 1991, pp. 295-298.

Melzack R, Wall PD; Pain mechanisms: a new theory; Science. 1965; 150(3699):971-979.

Tong KC, Lo SK, Cheing GL; Alternating frequencies of transcutaneous electric nerve stimulation: does it produce greater analgesic effects on mechanical and thermal pain thresholds; Archives of Physical Medicine and Rehabilitation, Oct. 2007;88(10): 1344-9.

Chen CC, Johnson MI; An investigation into the effects of frequency-modulated transcutaneous electrical nerve stimulation (TENS) on experimentally-induced pressure pain in healthy human participants; Journal of Pain, Oct. 2009;10(10):1029-37.

Yarnitsky D., Conditioned pain modulation (the diffuse noxious inhibitory control-like effect): its relevance for acute and chronic pain states; Current Opinion on Anaesthesiology, Oct. 2010;23(5):611-5.

Youssef A.M., V.G. Macefield V.G., Henderson L.A.; Pain inhibits pain; human brainstem mechanisms; NeuroImage 124 (2016) 54-62.

Marina De Tommaso, Olimpia Difruscolo, Michele Sardaro, Giuseppe Libro, Carla Pecoraro, Claudia Serpino, Paolo Lamberti, Paolo Livrea; Effects of remote cutaneous pain on trigeminal laser-evoked potentials in migraine patients; Journal of Headache Pain (2007) 8:167-174.

(56) References Cited

OTHER PUBLICATIONS

Ossipov M.H., Morimura K., Porreca F.; Descending pain modulation and chronification of pain; Current Opinion in Supportive & Palliative Care: Jun. 2014—vol. 8—Issue 2—p. 143-151.
U.S. Appl. No. 62/102,606, filed Jan. 13, 2015.
European Search Report issued in European Appl. No. 16737139.2, dated Sep. 18, 2018.

* cited by examiner

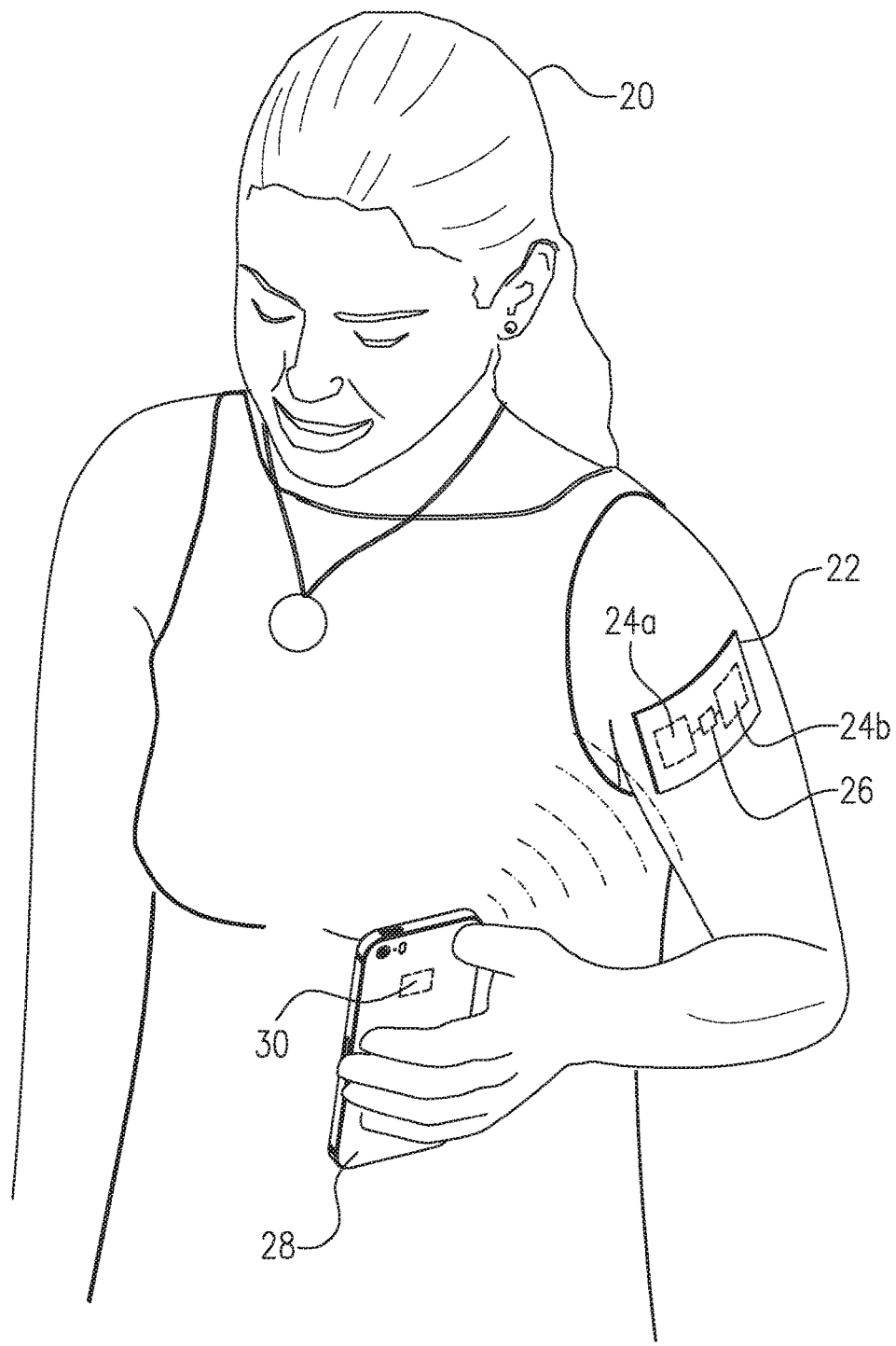

TREATMENT OF HEADACHES BY ELECTRICAL STIMULATION

CROSS-REFERENCE TO RELATED APPLICATIONS

This application is a U.S. national phase of International Application No. PCT/IB2016/050104, filed on Jan. 11, 2016, which claims priority to U.S. Provisional Application No. 62/102,606, filed Jan. 13, 2015, both of which are incorporated by reference herein in their entirety.

FIELD OF THE INVENTION

The present application relates to the field of transcutaneous electrical stimulation.

BACKGROUND

Migraine is a common neurovascular disorder manifesting itself in attacks of headaches that can reach a level of severe pain in many patients, leading to substantial functional impairment. The recent Global Burden of Disease Study 2010 (GBD2010), conducted by the World Health Organization, estimates a worldwide prevalence of migraine of 14.7%, ranking it third place among the most common diseases, seventh place among specific causes of disability, and top among neurological disorders as cause of total years lived with disability. Migraine, thus, affects millions of people. To date, the pathophysiology of migraine is not fully understood. The current approach to migraine treatment is predominantly pharmacological.

U.S. Pat. No. 8,340,771, whose disclosure is incorporated herein by reference, describes, according to one aspect, a method of treating a patient by electrically stimulating a predetermined site to treat a neurological condition. The method includes implanting a lead into subcutaneous tissue of the C2 dermatome/C3 dermatome area.

US Patent Publication 2014/0222102, whose disclosure is incorporated herein by reference, describes an application downloadable to a mobile device for facilitating muscle therapy, the applicable programmed and configurable to generate waveform signals, the waveform signals configured to be employed by a power circuit to generate energy, conforming to the signals, to a muscle pad. The application may be combined as a system with a muscle pad electrically interfacing with the downloadable application, as well as a discrete device in electrical communication with the mobile device and the muscle pad. A power circuit and a muscle metric feedback circuit are contemplated as part of embodiments of a system or kit.

US Patent Publication 2014/0194946, whose disclosure is incorporated herein by reference, describes a TENS apparatus that includes a portable TENS device having a housing with a lower surface, a pair of integral electrodes that are incorporated in the lower surface of the housing, and a pulse driver that is located within the housing and adapted to generate a program of pulse waveforms, each of which is an asymmetrical biphasic square waveform.

U.S. Pat. No. 8,880,173, whose disclosure is incorporated herein by reference, describes a device for providing transdermal electrical stimulation at an adjustable position on a head. The device includes a supporting member economically shaped and configured to be fixedly supported about an anatomical body part; the supporting member being adjustably positionable in only two directions substantially perpendicular to one another. No electrical stimulation is provided by the supporting member. Alternatively, the device includes at least one pair of electrodes for producing the transdermal electrical stimulation to the head. The electrodes are mounted to a securing member shaped and configured to be releasably securable only about a plurality of strands of hair at a predetermined fixed orientation without being secured about any anatomical body part.

U.S. Pat. No. 8,805,548, whose disclosure is incorporated herein by reference, describes a headband for use in neurostimulation made at least partly of elastic or stretch material comprising: a hole to be located directly on the rear part of the scalp of a user, said hole being sized to fit the inion or occipital protuberantia; at least two electrodes directly attached to the headband and positioned adjacent to and symmetric about said hole, designed so that to be applied on the right and left branch of the occipital nerve respectively, once the inion is put in correspondence with said hole by the user; a connector for connecting a wearable neurostimulator to the headband, said connector being located opposite to said hole, once the headband is worn by the user and means coupled to the elastic or stretch material for electrically connecting said connector and each of said electrodes.

U.S. Pat. No. 8,428,734, whose disclosure is incorporated herein by reference, describes a device for the electrotherapeutic treatment of headaches such as tension headaches and migraines. An electrode support has a shape and is size selected so as to allow, independently from the subject, the excitation of the afferent paths of the supratrochlear and supraorbital nerves of the ophthalmic branch of the trigeminal nerve. An electrical circuit includes a programmable signal generator suitable for creating pulses of a duration of between 150 and 450 microseconds with a maximum increase in intensity of 0 to 20 milliamperes at a rate of less than or equal to 40 microamperes per second and with a step up in intensity not exceeding 50 microamperes.

U.S. Pat. No. 8,874,205, whose disclosure is incorporated herein by reference, describes a non-invasive electrical stimulation device that shapes an elongated electric field of effect that can be oriented parallel to a long nerve, such as a vagus nerve in a patient's neck, producing a desired physiological response in the patient. The stimulator comprises a source of electrical power, at least one electrode and a continuous electrically conducting medium in which the electrode(s) are in contact. The stimulation device is configured to produce a peak pulse voltage that is sufficient to produce a physiologically effective electric field in the vicinity of a target nerve, but not to substantially stimulate other nerves and muscles that lie between the vicinity of the target nerve and patient's skin. Current is passed through the electrodes in bursts of preferably five sinusoidal pulses, wherein each pulse within a burst has a duration of preferably 200 microseconds, and bursts repeat at preferably at 15-50 bursts per second.

U.S. Pat. No. 8,874,227, whose disclosure is incorporated herein by reference, describes a non-invasive electrical stimulator that shapes an elongated electric field of effect that can be oriented parallel to a long nerve, such as a vagus nerve in a patient's neck, producing a desired physiological response in the patient. The stimulator comprises a source of electrical power, at least one electrode and a continuous electrically conducting medium in contact with the electrodes. The conducting medium is also in contact with an interface element that may conform to the contour of a target body surface of the patient when the interface element is applied to that surface. When the interface element is made of insulating (dielectric) material, and disclosed stimulation waveforms are used, the power source need not supply high voltage, in order to capacitively stimulate the target nerve. The stimulator is configured to produce a peak pulse that is sufficient to produce a physiologically effective electric field in the vicinity of a target nerve, but not to substantially stimulate other nerves and muscles that lie in the vicinity of the target nerve and patient's skin.

Slavin, Konstantin V., Hrachya Nersesyan, and Christian Wess. "Peripheral neurostimulation for treatment of intractable occipital neuralgia." Neurosurgery 58.1 (2006): 112-119, which is incorporated herein by reference, describes chronic peripheral nerve stimulation for long-term treatment of chronic pain syndrome in patients with medically intractable occipital neuralgia.

Ristic, Dejan, and Jens Ellrich. "Innocuous peripheral nerve stimulation shifts stimulus-response function of painful laser stimulation in man." Neuromodulation: Technology at the Neural Interface 17.7 (2014): 686-695, which is incorporated herein by reference, describes electrical peripheral nerve stimulation as an effective neuromodulatory treatment in chronic pain.

Nir, Rony-Reuven, et al. "A psychophysical study of endogenous analgesia: the role of the conditioning pain in the induction and magnitude of conditioned pain modulation." European Journal of Pain 15.5 (2011): 491-497, which is incorporated herein by reference, experimentally examines endogenous analgesia using a conditioned pain modulation paradigm.

Burstein, Rami, Michael F. Cutrer, and David Yarnitsky. "The development of cutaneous allodynia during a migraine attack clinical evidence for the sequential recruitment of spinal and supraspinal nociceptive neurons in migraine." Brain 123.8 (2000): 1703-1709, which is incorporated herein by reference, studied the way in which cutaneous allodynia develops by measuring the pain thresholds in the head and forearms bilaterally at several time points during a migraine attack in a 42-year-old male.

SUMMARY OF THE INVENTION

There is provided, in accordance with some embodiments of the present invention, a system for electrostimulation. The system includes a patch, including a plurality of electrodes, and a mobile device. A processor of the mobile device is configured to receive an input from a subject that indicates that the subject is experiencing a headache, and, in response to the input, while the patch is coupled to the subject, wirelessly communicate a control signal that causes the electrodes to stimulate the subject.

In some embodiments, the processor is further configured to:
obtain a physical location of the subject, and
in response thereto, present, on the mobile device, a migraine-related forecast that is specific to the physical location of the subject.

There is further provided, in accordance with some embodiments of the present invention, a method for treating a headache. A plurality of electrodes are coupled to a subject, caudally to a neck of the subject. In response to the subject experiencing a headache, using the coupled electrodes, without using any element that is implanted in the subject, and without using any element that penetrates skin of the subject, the headache is treated, by transcutaneously stimulating the subject.

In some embodiments, coupling the electrodes caudally to the neck of the subject includes coupling the electrodes to an arm of the subject.

In some embodiments, coupling the electrodes to the arm of the subject includes coupling the electrodes to an upper arm of the subject.

In some embodiments, coupling the electrodes to the arm of the subject includes coupling the electrodes transversely to the arm of the subject.

In some embodiments, transcutaneously stimulating the subject includes transcutaneously stimulating the subject by applying, to the subject, a plurality of electrical pulses.

In some embodiments, applying the electrical pulses includes applying the electrical pulses at a non-constant rate.

In some embodiments, applying the electrical pulses includes applying the electrical pulses at a rate of between 100 and 120 pulses per second.

In some embodiments, each of the electrical pulses has a duration of between 90 and 410 microseconds.

In some embodiments, transcutaneously stimulating the subject includes transcutaneously stimulating the subject for a total duration of between 1200 and 2600 seconds.

In some embodiments, the electrodes are coupled to an adhesive patch, and coupling the electrodes to the subject includes adhering the adhesive patch to the subject.

In some embodiments, the method further includes wirelessly communicating a control signal that causes the coupled electrodes to transcutaneously stimulate the subject.

In some embodiments, wirelessly communicating the control signal includes wirelessly communicating the control signal from a mobile device.

In some embodiments, the mobile device includes a mobile phone.

In some embodiments, the headache is a migraine headache.

In some embodiments, transcutaneously stimulating the subject includes transcutaneously stimulating the subject within two hours of the subject beginning to experience the headache.

In some embodiments, the method further includes controlling the stimulation of the subject in response to feedback received from the electrodes.

In some embodiments, the feedback includes an impedance measurement, and controlling the stimulation of the subject includes controlling the stimulation of the subject in response to the impedance measurement.

In some embodiments, the feedback includes an electromyographical measurement, and controlling the stimulation of the subject includes controlling the stimulation of the subject in response to the electromyographical measurement.

In some embodiments, transcutaneously stimulating the subject includes transcutaneously stimulating the subject using stimulation parameters derived by processing results of electrostimulation treatment of a plurality of other subjects.

There is further provided, in accordance with some embodiments of the present invention, a computer software product including a tangible non-transitory computer-readable medium in which program instructions are stored. The instructions, when read by a processor of a mobile device, cause the processor to receive an input from a subject that indicates that the subject is experiencing a headache, and, in response to the input, wirelessly communicate a control signal that causes a plurality of electrodes coupled to the subject to transcutaneously stimulate the subject.

In some embodiments, the input is a first input, and the instructions further cause the processor to receive one or more second inputs regarding a level of pain experienced by the subject, and, in response to the one or more second inputs, generate an output.

The present invention will be more fully understood from the following detailed description of embodiments thereof, taken together with the drawings, in which:

BRIEF DESCRIPTION OF THE DRAWINGS

FIG. 1 is a schematic illustration of a method for treating a headache, in accordance with some embodiments of the present invention.

DETAILED DESCRIPTION OF EMBODIMENTS

Overview

Transcutaneous electrical stimulation (or transcutaneous "electrostimulation") is a non-invasive technique that delivers a sequence of weak electrical pulses to a subject's skin. "Weak," in this context, means that the intensity of the pulses is typically below the pain threshold of the subject. Electrical stimulation is widely used to treat painful conditions, by the application of the above-mentioned weak pulses to the painful region of the body.

The present inventors have discovered that transcutaneous electrostimulation may be used to treat headaches, such as migraine headaches or tension headaches, even if the stimulation is not applied in the immediate vicinity of the painful region of the subject's body. For example, the stimulation may be applied caudally to the subject's neck, i.e., below the subject's neck, such as on the subject's torso, or on an arm or leg of the subject. The ascending stimulus-induced activity evokes descending pathways, which, in turn, exert modulatory effects on incoming nociceptive inputs, modifying the degree to which the headache is perceived. This underlying phenomenon, known as conditioned pain modulation, is described in the above-referenced article by Nir et al., which is incorporated herein by reference.

Further to the aforementioned discovery, embodiments of the present invention treat headaches, by delivering transcutaneous electrostimulation caudally to the neck of the subject. Typically, upon experiencing a headache, the subject adheres an adhesive patch to a suitable part of the subject's body, such as the subject's upper arm. The subject then uses a mobile device, such as the subject's mobile phone, to communicate a control signal that causes electrodes on the patch to deliver electrical stimuli to the subject.

The techniques described herein are particularly effective in treating migraine headaches. As described in the above-cited article to Burstein et al., the nociceptive pathways associated with the migraine headache undergo a process of sensitization during, approximately, the first two hours following the onset of the headache. Hence, by delivering electrostimulation treatment during these first two hours, the migraine headache may be aborted, or at least become reduced in severity.

As described below, clinical data collected by the inventors provide evidence that techniques described herein provide effective relief, without causing pain or other adverse side effects.

Another advantage of embodiments of the present invention is that the provided treatment is performed entirely non-invasively. In other words, no implanted or skin-penetrating element—i.e., no implanted or skin-penetrating device or any part of any device—is used to deliver the treatment. Moreover, since treatment is delivered caudally to the neck, rather than nearer to the actual pain site, embodiments described herein are significantly safer than some other methods that have been described. For example, methods that stimulate the trigeminal or vagus nerve (which are near the head) risk impacting important functions such as facial sensation, biting, chewing, heart rate, sweating, and speech. Embodiments described herein, on the other hand, do not run this risk.

Moreover, the patch is typically relatively small and disposable, and does not include cumbersome wired connections external to the patch. Hence, the patch may be worn for prolonged periods, and repeatedly activated when needed.

Method Description

Reference is initially made to FIG. 1, which is a schematic illustration of a method for treating a headache experienced by a subject 20, in accordance with some embodiments of the present invention.

To treat the headache, subject 20 first couples a plurality of electrodes to, for example, an arm of the subject. For example, as shown in the FIGURE, the subject may adhere a flexible adhesive patch 22 to her upper arm, adhesive patch 22 having a plurality of electrodes 24a and 24b coupled to the underside thereof. Subsequently, the electrodes transcutaneously stimulate the subject, by delivering electrical stimuli to the subject.

In some embodiments, as shown in the FIGURE, the electrodes are coupled transversely to the upper arm of the subject. In other embodiments, the electrodes are coupled proximally-distally, e.g., by adhering patch 22 in an orientation that is rotationally offset by 90 degrees from the orientation shown in FIG. 1. In yet other embodiments, other orientations may be used. In some embodiments, rather than adhering a patch to the subject, the subject wears a cuff, sleeve, or wrap around the subject's arm or leg, the cuff, sleeve, or wrap having a plurality of electrodes coupled thereto.

In some embodiments, the electrodes are coupled to a single dermatome. In other embodiments, the electrodes are spread over a plurality of dermatomes. Generally, factors that affect which dermatomes are stimulated include the size of the patch, the position and orientation of the patch, and the position of the electrodes on the patch.

Typically, an electronics module 26 contained within the patch controls the electrodes, in response to control signals, which are typically wirelessly received. Electronics module 26 typically comprises a power source, a central processing unit (CPU), typically programmed in microcode, that controls the electrodes, one or more memory units for storing the stimulation sequences during the stimulation, an impulse generator, and components for wireless communication, based on Bluetooth Low Energy (BLE) technology, for example. In some embodiments, the electronics module is an integrated system-on-chip (SoC).

Although only two electrodes are shown in FIG. 1, it is noted that any suitable number of electrodes may be used, sequentially or concurrently, to deliver electrostimulation pulses. Moreover, some of the electrodes coupled to the subject may be used for sensing, alternatively or additionally to being used for electrostimulation. For example, a single electrode pair may perform both stimulating and sensing functions. In response to the sensing, the electrodes provide feedback signals to the CPU. In response thereto, the CPU may automatically control the treatment, and/or transmit the feedback to a mobile device (as described below), which, in turn, may automatically control the treatment.

Typical sensing functions include the monitoring of electrode-skin impedance, as described, for example, in U.S. application Ser. No. 14/992,046, filed Jan. 11, 2016, which issued as U.S. Pat. No. 9,895,533 and is incorporated herein by reference. Such monitoring enhances the comfort and safety of the subject, by allowing the detection of electrode peel-off, and/or abnormal physiological reactions, such as excessive sweating. In response to impedance-related feedback from the electrodes, the treatment may be interrupted.

Alternatively or additionally, electromyographical sensing may be used to help set the appropriate stimulation intensity. For example, if muscle contractions are detected, the intensity may be automatically reduced, and/or the subject may be prompted (e.g., via a dedicated application running on the subject's mobile device) to reduce the intensity or re-position the patch.

Typically, as shown in the FIGURE, the electrodes begin to stimulate the subject in response to a wireless control signal, such as a wireless control signal from a mobile device 28. Upon receiving the control signal, the electronics module drives the electrodes to begin stimulating the subject.

In some embodiments, mobile device 28 comprises a smartphone or tablet comprising a processor 30, which is typically a programmed digital computing device comprising a central processing unit (CPU), random access memory (RAM), non-volatile secondary storage, such as a hard drive, network interfaces, and/or peripheral devices. Program code, including software programs, and/or data are loaded into the RAM for execution and processing by the CPU and results are generated for display, output, transmittal, or storage, as is known in the art. The program code and/or data may be downloaded to the processor in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

For example, a dedicated application running on the mobile device may provides program instructions which, when read by processor 30, cause processor 30 to perform the various tasks described herein. (For simplicity, the present description may refer to various tasks performed by the processor in response to such program instructions as being performed by "the application," "the dedicated application," or "the mobile application.") Typically, such an application provides instructions that cause the processor to receive an input from the subject that indicates that the subject is experiencing a headache, and, in response to the input, communicate the control signal to the electronics module.

In some embodiments, the dedicated application further allows the subject to choose a particular treatment program, and/or control stimulation parameters, such as the intensity of the stimulation. Alternatively or additionally, the application may monitor the treatment, by receiving feedback from the electrodes. In response to the feedback, the application may change the treatment program, adjust stimulation parameters (e.g., by adjusting the stimulation intensity in response to electromyographical feedback), or terminate the treatment (e.g., in response to the feedback indicating an abnormally high impedance at the electrode-skin interface).

In some embodiments, the application alternatively or additionally logs activity associated with the treatment, monitors historical activity, generates customized treatment programs, and/or generates customized reports for viewing by the subject and/or the subject's physician. In some embodiments, the application retrieves data from, and/or writes data to, the subject's electronic health records. Alternatively or additionally, the application may send data to a server for additional analysis, and/or for integration with existing data repositories, e.g., to expand collective knowledge. For example, the application may transmit the respective location of, and statistics related to, each treatment session, and such data may then be used to improve the accuracy of, and/or enrich the content of, location-specific migraine forecasts, as further described hereinbelow.

In some embodiments, the application updates the treatment programs offered to the subject, in response to receiving collective "wisdom of the crowd" feedback or information based on "big data" processing. For example, a remote server may process results from electrostimulation treatment of a plurality of other subjects, and the application may use, as the default stimulation parameters, stimulation parameters (including, for example, an intensity or duration of stimulation) derived from such processing.

In some embodiments, the application collects feedback from the subject. For example, the application may query the subject regarding the subject's level of pain prior to treatment, during the treatment, immediately following treatment, and/or some time after treatment (e.g., two hours post-treatment). Such feedback may be used to generate any relevant output, such as a customized report as described above, an output that recommends a particular adjustment of treatment parameters, or a control signal that adjusts the treatment parameters.

In some embodiments, the mobile application obtains, with the subject's approval, the subject's physical location coordinates, e.g., using a Global Positioning System (GPS) service. The application then obtains a migraine-related forecast, which is specific to the subject's location, from a relevant service, such as the AccuWeather.com Migraine Headache Forecast. The application may then present the forecast to the subject, thus informing the subject of the probability that the subject will experience a migraine attack during an upcoming period of time, e.g., during the next day and/or week. The application may enrich such a migraine forecast with treatment-related statistics collected from a plurality of subjects, as described above. For example, the application may increase the risk level for the subject's location if a relatively large number of treatments have recently been recorded in the subject's location.

Alternatively or additionally, the mobile application may generate various warnings, alerts, reminders, or other types of output, which may be delivered to the subject in audio and/or visual form. For example, in response to a threatening migraine forecast, the mobile application may suggest that the subject remain at home on a particular day, or at least refrain from traveling to a particular location. Alternatively or additionally, in response to a threatening forecast, the mobile application may remind the subject to bring along the subject's patch, in case treatment will be required.

Alternatively or additionally, if the power source within electronics module 26 is running low, the application may remind the subject to recharge the power source, or obtain a new patch.

Typically, as noted above, electronics module 26 comprises one or more memory units, such as Random Access Memory (RAM) units. The memory units store the stimulation sequences during the stimulation, such that the mobile device need not necessarily remain in communication with the patch during the treatment.

In some embodiments, to establish the connection between device 28 and patch 22, the subject inputs an identifying field, such as a username, to the device. Alternatively or additionally, the device may identify the patch by scanning a barcode or other suitable identifier on the patch, and/or by capturing an image of the patch and identifying the patch in the image.

In some embodiments, patch 22 may be additionally used for the controlled delivery of medications, such as pain relief medications or antidepressants. The application running on device 28 may control such delivery, in response to feedback from the electrodes.

In some embodiments, the above-described techniques are used to prevent the onset of headaches, before any pain is sensed by the subject. For example, a customized electrostimulation treatment as described above may be delivered at regular intervals, e.g., daily. The dedicated application on mobile device 28 may facilitate the scheduling of such treatments, and/or may automatically alert the subject when necessary, in order to facilitate compliance with the treatment schedule.

Stimulation Parameters

Although the scope of the present disclosure includes using any relevant stimulation parameters, the present inventors have found that certain stimulation parameters may be particularly effective in treating migraine headaches.

One parameter is the rate (or "frequency") at which the plurality of electrical pulses are applied to the subject. The inventors have found that a rate of between 100 and 120 pulses per second (which may be expressed as a frequency of between 100 and 120 Hz) may be particularly effective. In some embodiments, the electrical pulses are applied at a non-constant rate. For example, the rate of pulse delivery may vary within the range of between 100 and 120 pulses per second over the course of the stimulation. Such variation in pulse rate may help prevent habituation of the central nervous system to the stimulation.

Another parameter is the duration (or "width") of each pulse. The inventors have found that a pulse duration of between 90 and 410 microseconds may be particularly effective. In particular, the inventors have defined three stimulation programs, each of which uses a different respective pulse duration: "program 1" uses a pulse duration of 200 microseconds, "program 2" uses 300 microseconds, and "program 3" uses 400 microseconds. Each of the above programs has a total stimulation duration of 1200 to 2600 seconds, and a pulse rate that varies in the range of between 100 and 120 pulses per second.

Typically, the pulse duration does not vary over the course of the stimulation. Each pulse typically has a symmetric, square shape, comprising positive and negative portions of equal duration. Thus, for example, in program 1, each of the positive and negative portions of each pulse has a duration of 100 microseconds.

Another parameter is the intensity of the pulses. This parameter is typically set separately by and/or for each subject, such that each subject is stimulated at an intensity that is slightly below the subject's pain threshold. As described above, the dedicated application running on mobile device 28 may help set the intensity, by receiving relevant feedback from the subject.

Clinical Data

In a study performed at Rambam Hospital, Haifa, Israel, a plurality of subjects were treated for migraine headaches, using techniques described herein. In particular, 129 treatments were performed using program 3 as defined above, 54 treatments were performed using program 2, and 46 treatments were performed using program 1. 35 placebo treatments were also performed. The results for program 3 are presented below. (For simplicity, the results for the other two programs—which, like the results for program 3, reflect favorably on the presently-disclosed techniques—are not included in the present disclosure.)

For 42% of treatments (vs. only 29% for the placebo), the treated subject reported significant pain relief two hours after treatment. For 17% of treatments (vs. only 9% for the placebo), the treated subject reported complete pain relief two hours after treatment. Moreover, 34% of the 32 treated subjects (vs. only 7% of the 15 placebo-treated subjects, and only 29% of subjects treated with Sumatriptan, a common medication used for migraine treatment) reported, on average, complete pain relief two hours after treatment.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
coupling a plurality of electrodes to skin of a lateral surface of an upper arm of a subject; and
using a computer processor, in response to the subject experiencing a headache, without using any element that is implanted in the subject, and without using any element that penetrates skin of the subject, treating the headache, by transcutaneously stimulating the subject, by applying an electrical current to the skin, via the electrodes.

2. A method, comprising:
coupling a plurality of electrodes to a location of a body of a subject selected from the group consisting of: skin of an upper arm of the subject, and skin of a leg of the subject; and
using a computer processor, in response to the subject experiencing a headache, without using any element that is implanted in the subject, and without using any element that penetrates skin of the subject, treating the headache, by transcutaneously stimulating the subject, by applying a plurality of electrical pulses to the selected location, via the electrodes, at a rate of between 100 and 120 pulses per second.

3. The method according to claim 1, wherein transcutaneously stimulating the subject comprises applying a plurality of electrical pulses to the skin, via the electrodes.

4. The method according to claim 3, wherein applying the electrical pulses comprises applying the electrical pulses at a non-constant rate.

5. The method according to claim 3, wherein applying the electrical pulses comprises applying the electrical pulses, each of the electrical pulses having a duration of between 90 and 410 microseconds.

6. The method according to claim 1, wherein transcutaneously stimulating the subject comprises transcutaneously stimulating the subject using a stimulation program having a total duration of between 1200 and 2600 seconds.

7. The method according to claim 1, wherein the electrodes are coupled to an adhesive patch, and wherein coupling the electrodes to the skin comprises adhering the adhesive patch to the skin.

8. The method according to claim 1, wherein, using the computer processor, transcutaneously stimulating the subject comprises wirelessly communicating a control signal that causes the coupled electrodes to transcutaneously stimulate the subject.

9. The method according to claim 8, wherein wirelessly communicating the control signal comprises wirelessly communicating the control signal from a mobile device.

10. The method according to claim 9, wherein the mobile device includes a mobile phone, and wherein wirelessly communicating the control signal comprises wirelessly communicating the control signal from the mobile phone.

11. The method according to claim 1, wherein the headache includes a migraine headache, and wherein treating the headache comprises treating the migraine headache, by transcutaneously stimulating the subject.

12. The method according to claim 1, wherein transcutaneously stimulating the subject comprises transcutaneously stimulating the subject within two hours of the subject beginning to experience the headache.

13. The method according to claim 1, further comprising, using the computer processor:
receiving feedback from the electrodes, and
controlling the stimulation of the subject in response to the feedback received from the electrodes.

14. The method according to claim 13, wherein receiving the feedback from the electrodes comprises receiving an impedance measurement from the electrodes, and wherein controlling the stimulation of the subject comprises controlling the stimulation of the subject in response to the impedance measurement.

15. The method according to claim 13, wherein receiving the feedback from the electrodes comprises receiving an electromyographical measurement from the electrodes, and wherein controlling the stimulation of the subject comprises controlling the stimulation of the subject in response to the electromyographical measurement.

16. The method according to claim 1, wherein treating the headache, in response to the subject experiencing the headache, comprises, using the computer processor:
receiving an input from the subject indicating that the subject is experiencing a headache; and
treating the headache, in response to receiving the input.

17. The method according to claim 1, wherein the headache includes a tension headache, and wherein treating the headache comprises treating the tension headache, by transcutaneously stimulating the subject.

18. A method, comprising:
coupling a plurality of electrodes to skin of an upper arm of a subject; and
using a computer processor, in response to the subject experiencing a headache, without using any element that is implanted in the subject, and without using any element that penetrates skin of the subject, treating the headache, by transcutaneously stimulating the subject, by applying an electrical current to the skin, via the electrodes,
wherein coupling the electrodes to the upper arm of the subject comprises coupling the electrodes transversely to the upper arm of the subject.

19. The method according to claim 18, wherein the electrodes are coupled to an adhesive patch, and wherein coupling the electrodes to the skin comprises adhering the adhesive patch to the skin.

20. The method according to claim 18, wherein the headache includes a migraine headache, and wherein treating the headache comprises treating the migraine headache, by transcutaneously stimulating the subject.

21. The method according to claim 2, wherein coupling the electrodes to the selected location comprises coupling the electrodes to the upper arm of the subject.

22. The method according to claim 2, wherein the headache includes a migraine headache, and wherein treating the headache comprises treating the migraine headache, by transcutaneously stimulating the subject.

23. Apparatus for use with a subject, the apparatus comprising:
a plurality of electrodes configured to be coupled to a location selected from the group consisting of: skin of an upper arm of the subject, and skin of a leg of the subject; and
a computer software product comprising a tangible non-transitory computer-readable medium in which program instructions are stored, which instructions, when read by a processor of a mobile device, cause the processor to:
receive an input from a subject that indicates that the subject is experiencing a headache, and
in response to the input, wirelessly communicate a control signal that causes the plurality of electrodes to transcutaneously stimulate the subject by applying a plurality of electrical pulses to the selected location, via the electrodes, at a rate of between 100 and 120 pulses per second.

24. The apparatus according to claim 23, further comprising an adhesive patch, the electrodes being disposed upon the adhesive patch and being configured to be coupled to the selected location by the adhesive patch being adhered to the selected location.

* * * * *